United States Patent

Dang

[11] Patent Number: 5,843,168
[45] Date of Patent: Dec. 1, 1998

[54] DOUBLE WAVE STENT WITH STRUT

[75] Inventor: Kenny L. Dang, San Diego, Calif.

[73] Assignee: Medtronic, Inc., Minneapolis, Minn.

[21] Appl. No.: 828,612

[22] Filed: Mar. 31, 1997

[51] Int. Cl.[6] ....................................................... A61F 2/06
[52] U.S. Cl. .............................. 623/1; 623/12; 606/194; 606/198
[58] Field of Search .......................... 623/1, 12; 606/191, 606/194, 198

[56] References Cited

U.S. PATENT DOCUMENTS

| 4,856,516 | 8/1989 | Hillstead | 128/343 |
| 4,878,906 | 11/1989 | Lindemann et al. | 623/1 |
| 4,886,062 | 12/1989 | Wiktor | 128/343 |
| 4,994,071 | 2/1991 | MacGregor | 606/194 |
| 5,061,275 | 10/1991 | Wallsten et al. | 623/1 |
| 5,104,404 | 4/1992 | Wolff | 623/1 |
| 5,116,365 | 5/1992 | Hillstead | 623/12 |
| 5,133,732 | 7/1992 | Wiktor | 606/195 |
| 5,135,536 | 8/1992 | Hillstead | 606/195 |
| 5,195,984 | 3/1993 | Schatz | 606/195 |
| 5,366,504 | 11/1994 | Andersen et al. | 623/1 |
| 5,389,106 | 2/1995 | Tower | 606/198 |
| 5,618,298 | 4/1997 | Simon | 606/194 |
| 5,643,339 | 7/1997 | Kavteladze et al. | 623/12 |

FOREIGN PATENT DOCUMENTS

| 0645125 | 3/1995 | European Pat. Off. . |
| 9412136 | 6/1994 | WIPO . |

Primary Examiner—Paul B. Prebilic
Attorney, Agent, or Firm—Dianne M. Plunkett; Harold R. Patton

[57] ABSTRACT

A radially expandable stent for implantation within a body vessel, comprising a first and second elongated element having a series of peaks alternating with valleys forming a wave shape therein. The first elongated element is interwoven with the second elongated element in a series of crossovers, with each crossover forming a symmetrical intersection and each successive pair of crossovers defining a loop. The interwoven first and second elongated elements are wound into a hollow cylindrical shape with at least one longitudinal strut extending parallel to a longitudinal axis of the hollow cylindrical shape and passing through at least one of the loops along the hollow cylindrical shape.

15 Claims, 3 Drawing Sheets

DOUBLE WAVE STENT WITH STRUT

FIELD OF THE INVENTION

The present invention relates to intravascular stent implants for maintaining vascular patency in humans and animals and more particularly to a stent in the form of a double wave stent with strut.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the interior of the body lumen thereby forming a supporting relationship with the vessel walls.

The biocompatible metal stent props open blocked coronary arteries, keeping them from reclosing after balloon angioplasty. A balloon of appropriate size and pressure is first used to open the lesion. The process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn. A high pressure balloon is preferable for stent deployment because the stent must be forced against the artery's interior wall so that it will fully expand thereby precluding the ends of the stent from hanging down into the channel encouraging the formation of thrombus.

Various shapes of stents are known in the art. They may be a wire stent or a tubular stent and configured with or without struts. Prior art stents have struts and crossovers which are typically welded or formed integrally with the stent or permit only a limited range of movement. Such struts or crossovers may have more structural radial stiffness and lack flexibility in tortuous anatomies. Due to the dynamic motions of the arteries during the cardiac cycles, especially coronary arteries, stiffer stents may be more prone to fatigue and fracture.

U.S. Pat. No. 4,856,516 to Hillstead for "Endovascular Stent Apparatus and Method" discloses a wire first bent into a series of tight bends. The wire is then further bent into a sequence of loops that are connected by half hitch junctions and interconnections which are either aligned or spiral around the circumference of the stent.

U.S. Pat. No. 4,878,906 to Lindemann et al. for "Endoprosthesis for Repairing a Damaged Vessel" discloses a flexible, plastic, thin-walled sleeve molded with various types of circumferential and axial ribs and reinforcements to be used as an endovascular prosthesis. FIGS. 3, 5, 6, 8, and 9 disclose a fixed axial rib.

U.S. Pat. No. 4,886,062 to Wiktor for "Intravascular Radially Expandable Stent and Method of Implant" discloses a two-dimensional zig-zag form, typically a sinusoidal form and without longitudinal struts.

U.S. Pat. No. 4,994,071 to MacGregor for "Bifurcating Stent Apparatus and Method" discloses a wire forming a backbone extending axially along the length of the lattice that extends away from the lattice and is used to construct the interconnecting loops. A series of generally parallel oriented loops interconnected by a sequence of half-hitch connections extend along an axial dimension.

U.S. Pat. No. 5,061,275 to Wallsten for "Self-Expanding Prosthesis" discloses a number of elements having the same direction of winding but being axially displaced relative to each other and crossing a number of elements also axially displaced relative to each other but having the opposite direction of winding to form a braided structure.

U.S. Pat. No. 5,104,404 to Wolff for "Articulated Stent" discloses a stent made up of a number of wires welded together and then connected together with hinges to provide articulation.

U.S. Pat. No. 5,133,732 to Wiktor for "Intravascular Stent" discloses a stent body coiled from a generally continuous wire with a deformable zig-zag structure with a means for preventing the stent body from stretching along its longitudinal axis. A longitudinal wire is attached, preferably by welding to waves of wire at points.

U.S. Pat. No. 5,135,536 to Hillstead for "Endovascular Stent and Method" discloses locations permanently adhered together to form junctions which are generally aligned to form a backbone. Filament portions at each end and location 24 are permanently adhered together to form junctions to prevent the unrolling of the stent.

U.S. Pat. No. 5,195,984 to Schatz for "Expandable Interluminal Graft" discloses a plurality of slots disposed substantially parallel to the longitudinal axis of the tubular members, and adjacent grafts are flexibly connected by a single connector member disposed substantially parallel to the longitudinal axis of the tubular members. Connector members are preferably formed of the same material as grafts and may be formed integrally between adjacent grafts. The end turn of the helix is welded and intermediate welds are formed to stabilize the length of the helix.

U.S. Pat. No. 5,389,106 to Tower for "Impermeable Expandable Indovascular Stent" discloses a pigtail that is passed back along the circumferential sections and is joined to the other end section.

Commonly owned co-pending U.S. Ser. No. 08/633,394 to Boyle for "Joined Sinusoidal Helix Stent" discloses a sinusoidal wave stent which aligns at the off peak to the off valley adjacent locations with a pattern of welds affixing the alignment locations to each other.

Commonly owned co-pending U.S. Ser. No. 08/563,715 to Boyle et al. for "Interwoven Dual Sinusoidal Helix Stent" discloses braided peaks and valleys forming a braided region.

What is needed is a flexible stent design which overcomes the prior art inflexibility resulting from welding or twisting junctions at the crossovers of wires yet does not lengthen or shorten when used in tortuous anatomies and which has good coverage without being prone to fracture or fatigue as a result of repeated flexions with an artery.

SUMMARY OF THE INVENTION

The present invention is accomplished by providing a radially expandable stent for implantation within a body vessel, comprising a first and second elongated element having a series of peaks alternating with valleys forming a wave shape therein. The first elongated element is interwoven with the second elongated element in a series of crossovers, with each crossover forming a symmetrical intersection and each successive pair of crossovers defining a loop. The interwoven first and second elongated elements are wound into a hollow cylindrical shape with at least one longitudinal strut extending parallel to a longitudinal axis of the hollow cylindrical shape and passing through at least one of the loops along the hollow cylindrical shape.

DETAILED DESCRIPTION OF THE PREFERRED EMBODIMENTS

The double wave stent is designed to be flexible and to have high fatigue and fracture resistance while at the same time conforming to the dynamic motions of the arteries. It also avoids lengthening and shortening of the stent upon expansion. Applicant's crossovers 75 are not fixed points between the first wire segment 15 and the second wire segment 25. Strut 20 is affixed only at its proximal and distal end. This lack of fixation reduces the possibility of fracture and fatigue while increasing stent flexibility in tortuous anatomies.

Figure 1:
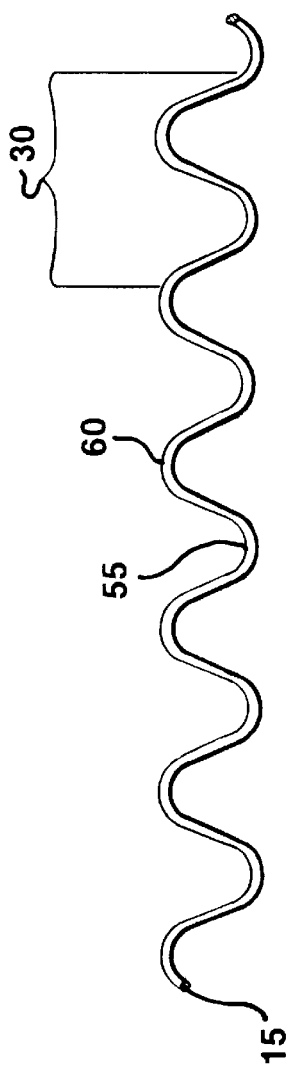
FIG. 1 is a plan view of a first wire segment.
Figure 2:
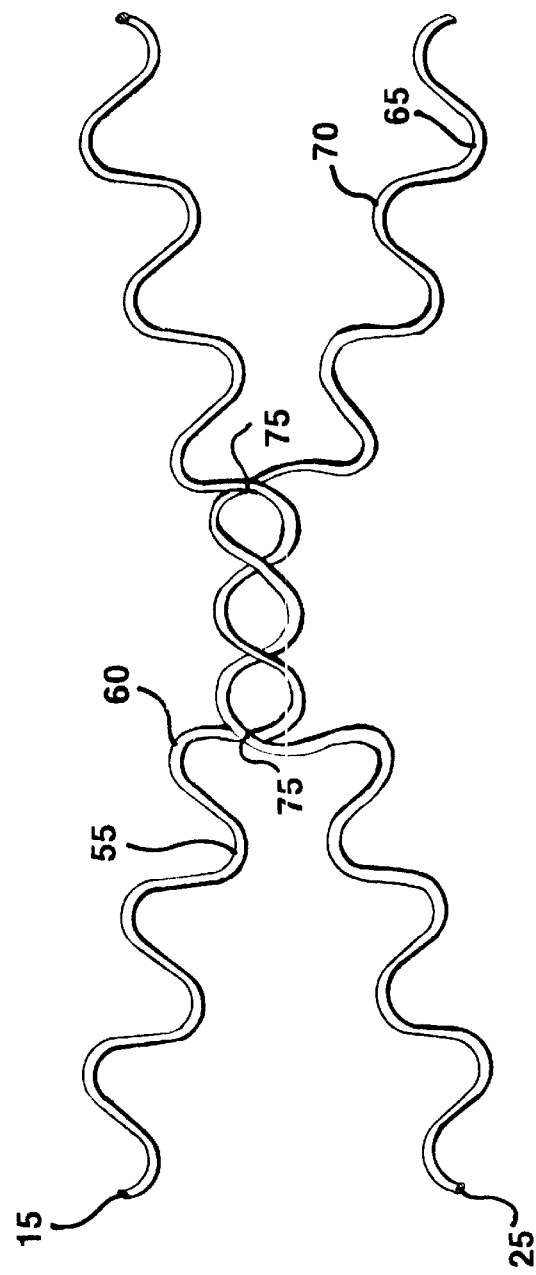
FIG. 2 is a plan view of a first and second wire segment showing four crossovers.

A typical stent is formed with a wire segment which is formed into a sinusoidal wave form helix pattern the length of the stent by a means such as passing the wire through gears such as those disclosed in U.S. Pat. No. 2,153,936 issued to Owens et al. As shown in FIGS. 1 and 2 a first wire segment 15 and a second wire segment 25 are formed into a sinusoidal wave form Helix pattern.

The first wire segment 15 is crossed over the second wire segment 25 at a point midway between a peak 60, 70 and valley 55, 65 Each peak 60, 70 and valley 55, 65 pair form a wave 30. The valleys of the first wire segment 15 are aligned along the same longitudinal axis as the valleys of the second wire segment 25. The peaks of the first wire segment 15 are aligned along the same longitudinal axis as the peaks of the second wire segment 15. The crossovers 75 of the first wire segment 15 alternate going over and under the second wire segment 25. The first wire segment 15 and the second wire segment 25 are not affixed to each other at crossovers 75. Unlike the prior art with welded or twisted crossovers, the wires are able to slide over each other causing less fatigue and potential fracture as arteries such as the coronary arteries flex.

Figure 3:
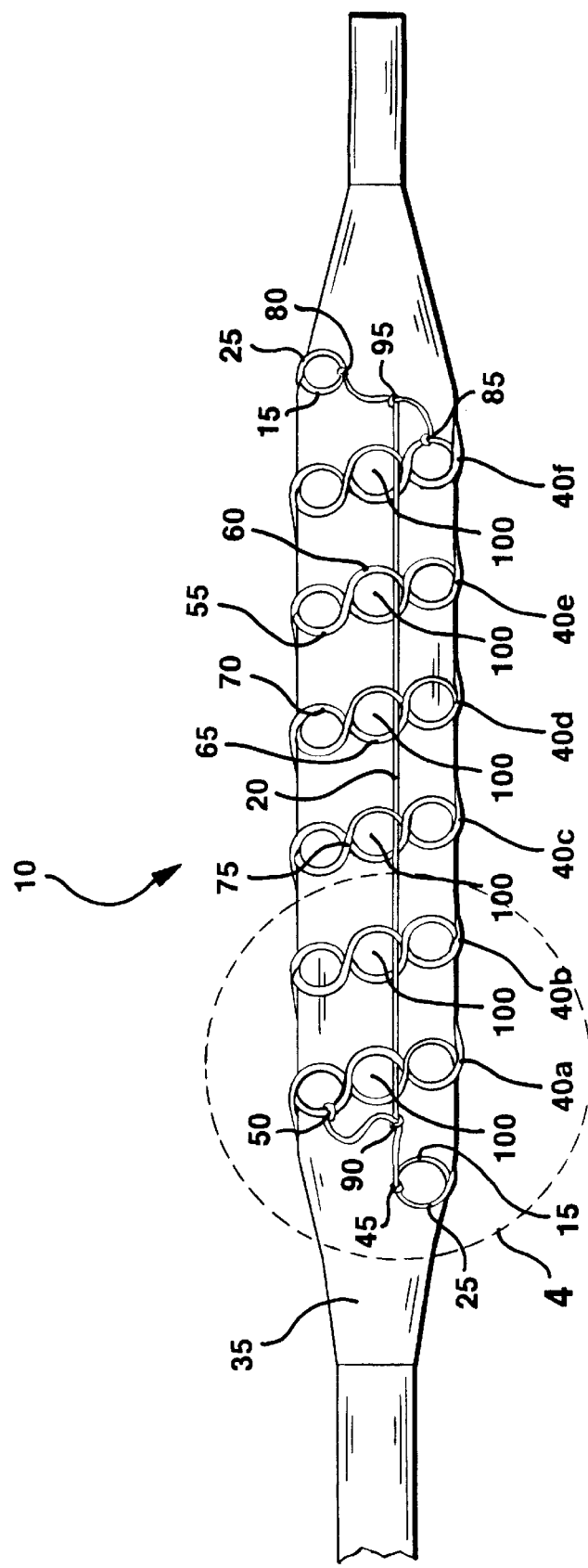
FIG. 3 is a plan view of a stent of the present invention mounted on a balloon catheter.
Figure 4:
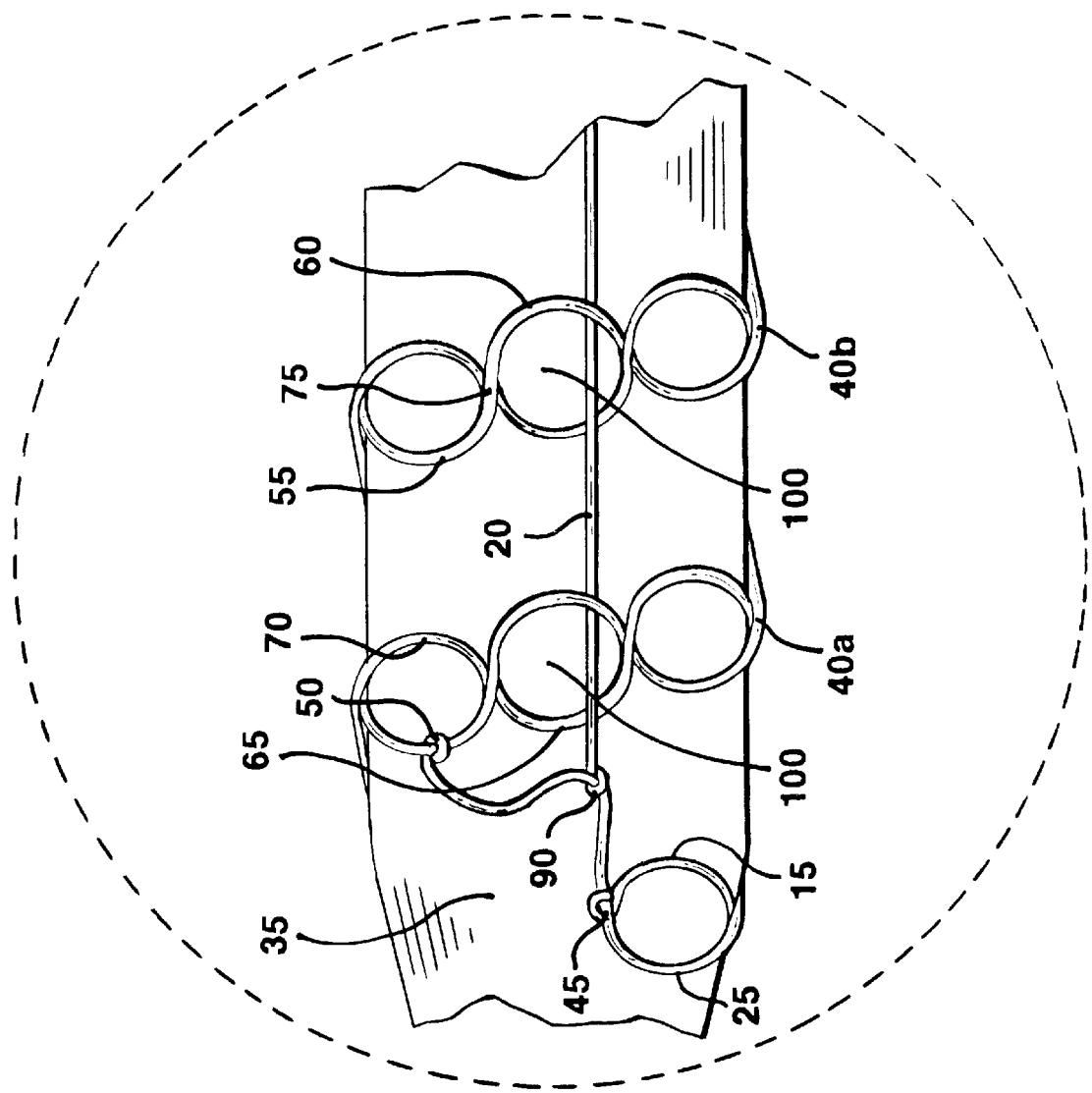
FIG. 4 is an enlargement of area 4 of FIG. 3.

After the crossovers 75 are created, the helix is wound in barber pole fashion over a cylindrical form such as a mandrel. The present invention shown in FIG. 3, depicts a radially expandable stent 10 in the form of a hollow cylinder defined by a sequence of wire elements 40a–f with each of the wire elements 40a–f extending 360 degrees around the cylinder. A peak 60, 70 and valley 55, 65 pair constitute a wave. Three to four waves per 360 degree revolution constitute an element 40 and are preferred for coronary applications. Applicant's invention is not limited to coronary applications, however, and can, for example, be used in peripheral and other applications. Those skilled in the art would recognize that the number of waves per revolution depends on the diameter of the stent and the desired stiffness.

The wire elements 40a–f have extendible, sinusoidal zig-zags formed by smooth bends such as alternating peaks 60 and valleys 55. As shown, the peaks 60 and valleys 55 are shaped in a generally longitudinal direction along the cylinder at one point and then reverse their direction so that the peaks 60 and valleys 55 may open as the wire element 40a is expanded. Also as shown, the wire elements 40a–f are uniformly spaced along the cylinder and the peaks 60 and valleys 55 are uniformly spaced around the cylinder. The adjacent wire elements 40a–f are flexibly connected together in an end-to-end fashion by means of helical winding. The wire elements 40a–f have a plurality of extendible portions, such as peaks 60 and valleys 55 which permit the wire elements to be expanded from a first diameter covering 360 degrees of the cylinder to a second, expanded diameter covering 360 degrees of the expanded cylinder.

A typical coronary stent may have the following dimensions. The stent wire 15 can have a diameter of about 0.001 inches to about 0.015 inches. The preferred form of the sinusoidal wave of the wire segment is a length of about 0.150 inches to about 0.090 inches and a wave amplitude of between about 0.050 inches and about 0.080 inches. Any wave length and amplitude combination that would provide adequate vessel 50 hoop strength and vessel 50 coverage is appropriate. The stent 10 must expand evenly and permit the balloon 35 to expand evenly. The stent 10 of this invention and balloon can be transported via a standard #7 or #8 French guiding catheter. Once on location, the stent 10 can be expanded radially by the expansion of the balloon 35; a ratio of 2.75:1 can be achieved with a wire diameter of approximately 0.005 inches and an initial stent diameter of 0.060 approximately inches.

A forming mandrel sequence can provide a gradual reduction in the stent 10 outer diameter by the use of applied finger pressure under microscopic observation. For a coronary sized stent it is possible to go directly from a 0.150 inch stent outer diameter to a 0.065 inch stent outer diameter by placing stent 10 directly onto the balloon 35 from the forming mandrel and make an acceptable stent, but it is more difficult to maintain proper alignment of the stent wires by doing so. Thus it is preferred that the stent 10 is further processed from a 0.150 inch diameter forming mandrel by pressing it onto a 0.100 inch diameter forming mandrel, thereafter pressing it onto a 0.080 inch diameter forming mandrel and finally pressing it onto a 0.065 inch diameter forming mandrel before being applied to the balloon 35. Those skilled in the art would recognize that a variety of acceptable mandrel sizes could be used in the forming sequence depending on the desired stent size.

After the stent 10 has been reduced to the objective outer diameter, the stent is terminated as follows. The proximal end of the first wire segment 15 is attached to the second wire segment 25. The proximal end of the second wire segment is attached to the closest adjoining element 40–*a*. The distal end of the first wire segment 15 is attached to the second wire segment 25. The distal end of the second wire segment is attached to the closest adjoining element 40-*f*.

Strut 20 is affixed by attaching the proximal end to a location on the second wire segment 25 distal to the first wire segment proximal loop attachment 45 to form the strut proximal loop attachment 90. The distal end of strut 20 is threaded through loops 100 parallel to the longitudinal axis of the stent 10. The distal end of strut 20 is then attached to a location on the second wire segment 25 distal to the first wire segment distal loop attachment 80 to form the strut distal loop attachment 95. The proximal end of the first wire segment 15 is terminated by affixing it to the second wire segment 25 to form the first wire segment proximal loop attachment 45. The distal end of the first wire segment 15 is terminated by affixing it to the second wire segment 25 to form the first wire segment distal loop attachment 80. The second wire segment 25 proximal end is terminated by affixing it to the closest adjoining element 40a to form the second wire segment proximal loop attachment 50. The second wire segment 25 distal end is terminated by affixing it to the closest adjoining element 40f to form the second wire segment distal loop attachment 85.

The attachments 45, 50, 80, 85, 90 or 95 could be done by manually looping them. Those skilled in the art will recognize other means of end attachments which include twisting, biocompatible adhesive, brazing, crimping, welding or stamping. The strut 20 can be attached either before or after the forming mandrel sequence. It is however, easier to form the strut after the forming mandrel sequence has reduced the stent 10 to its objective size.

Applicant's strut 20 is free to move within loops 100 with the dynamics of artery movement thereby resulting in less fatigue and fracture potential. Prior art struts which are welded or integral have more structural radial stiffness but lack flexibility in tortuous anatomies. The stiffer the stent, the more prone it is to fatigue and fracture. Applicant's strut 20 is not affixed except at the proximal and distal ends. It is free to flex in tortuous anatomies yet provides additional coverage. Applicant's strut 20 controls longitudinal deformation by resisting shortening or elongation of the stent 10 during expansion or compression because it is affixed at its proximal and distal ends. The free floating strut 20 slides freely between waves 30 yet adds radial (hoop) stiffness. Additional longitudinal stiffness and arterial support can be achieved by adding additional struts 20 through a series of loops 100 running longitudinally throughout the stent 10.

The balloon expandable stent 10 can be made of an inert, biocompatible material with high corrosion resistant that can be plastically deformed at low-moderate stress levels such as tantalum, the preferred embodiment. Other acceptable materials include stainless steel, titanium ASTM F63-83 Grade 1, niobium or high carat gold K 19–22. A self-expanding device can be made by the use of superelastic (nickel titanium) NiTi such as Nitinol manufactured by Raychem or Forukawa. The struts 20 can be made of a different material and/or be of a different diameter than the first wire segment 15 and second wire segment 25.

After formation, the stent 10 is placed over a suitable expandable diameter device such as an inflatable balloon 35 which is typically used for angioplasty procedures. A stent can be implanted during a single angioplasty procedure by using a balloon catheter bearing a stent 10 which has been crimped by hand or with a suitable crimping tool (not shown) onto balloon 35. Manually squeezing the stent 10 over the balloon 35 is also acceptable. The stent 10 is radially expanded as the balloon 35 is inflated, causing the stent 10 to contact the body lumen thereby forming a supporting relationship with the vessel walls. As the balloon 35 expands, so does the stent 10. The expanding balloon 35 together with the stent 10 compresses the plague in the stenosis and prevent possible reocclusion. When the angioplasty procedure is completed, the balloon 35 is deflated and withdrawn leaving the stent 10 firmly implanted within the vessel. The previously occluded vessel is recannalized and patency is restored. Any protrusions are undesirable because they are conducive to turbulent blood flow and potential formation of thrombosis. The stent 10 is centrally located and positioned with respect to the length of balloon 35. The stent 10 turns are evenly spaced so that when the stent 10 is expanded, the stent 10 will provide even support inside the vessel and resist external loading.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Stent |
| 15 | First Wire Segment |
| 20 | Strut |
| 25 | Second Wire Segment |
| 30 | Wave |
| 35 | Balloon |
| 40a–f | Element |
| 45 | First Wire Segment Proximal Loop Attachment |
| 50 | Second Wire Segment Proximal Loop Attachment |
| 55 | Valley First Wire Segment |
| 60 | Peak First Wire Segment |
| 65 | Valley Second Wire Segment |
| 70 | Peak Second Wire Segment |
| 75 | Crossover |
| 80 | First Wire Segment Distal Loop Attachment |
| 85 | Second Wire Segment Distal Loop Attachment |
| 90 | Strut Proximal Loop Attachment |
| 95 | Strut Distal Loop Attachment |
| 100 | Loop |

What is claimed is:

1. A radially expandable stent for implantation within a body vessel, comprising:

a first elongated element having a series of peaks alternating with valleys forming a wave shape therein;

a second elongated element having a series of peaks alternating with valleys forming a wave shape therein;

the first elongated element being interwoven with the second elongated element in a series of freely moving crossovers in a longitudinal direction and in a hoop direction, each crossover forming a symmetrical unaffixed intersection such as the stent is expandable from a first radial diameter to a second radial diameter;

each successive pair of crossovers defining a loop;

the interwoven first and second elongated elements being wound into a hollow cylindrical shape; and at least one longitudinal strut extending parallel to a longitudinal axis of the hollow cylindrical shape and passing through at least one loop along the hollow cylindrical shape.

2. The stent according to claim 1 wherein the first and second elongated elements are formed of a biocompatible metal that can be plastically deformed as the stent is radially expanded from a first compressed diameter to a second expanded diameter.

3. The stent according to claim 1 wherein the interwoven first and second elongated elements are wound in a helix to form the hollow cylindrical shape.

4. The stent according to claim 1 wherein an end of the first elongated element is attached to a portion of the second elongated element.

5. The stent according to claim 1 wherein the hollow cylindrical shape includes a series of loop extending 360 degrees around the hollow cylindrical shape such that the loop becomes elongated as the stent is expanded from a first, compressed radius to a second expanded radius.

6. The stent according to claim 1 wherein an end of the strut is attached to a portion of at least one of the first and second elongated elements at an end of the hollow cylindrical shape.

7. The stent according to claim 1 wherein the first and second elements are able to move and slide with respect to each other at a plurality of the crossover as a mechanical force is applied to the stent.

8. The stent according to claim 1 wherein the strut is able to move and slide with respect to the loop as a mechanical force is applied to the stent.

9. A radially expandable stent for implantation within a body vessel, comprising:

a first wire having a performed series of peaks alternating with valleys therein each peak and valley pair forming a wave, the first wire having a proximal end and a distal end;

a second wire having a performed series of peaks alternating with valleys therein, the second wire having a proximal end and a distal end;

the first wire being interwoven the second wire such that a series of freely moving crossovers in a longitudinal direction and in a hoop direction, is formed wherein the first wire and the second wire alternate being on top of the other with the crossovers occurring half way between the peak and valley of the first wire segment and the peak and valley of the second wire segment thereby forming symmetrical unaffixed intersections such that the stent is expandable from a first radial diameter to a second radial diameter;

each successive pair of crossovers defining a loop;

the interwoven first and second wires being wound into a continuous helix having a hollow cylindrical shape with each 360 degree series of loops constituting an element; and at least one longitudinal strut having a proximal end and a distal end, the strut extending parallel to a longitudinal axis of the hollow cylindrical shape and passing through at least one loop along the hollow cylindrical shape.

10. The stent according to claim 9 wherein the first and second wires are formed of a biocompatible metal that can be plastically deformed as the stent is radically expanded from a first compressed diameter to a second expanded diameter.

11. The stent according to claim 9 having a means within the interwoven first and second wires of the continuous helix for expanding the interwoven first and second wires of the continuous helix.

12. The stent according to claim 9 wherein the proximal end of the first wire segment is attached to the second wire segment forming a first wire proximal loop attachment, the proximal end of the second wire segment is attached to the first wire segment of an adjoining element or to the second wire segment of an adjoining element forming a second wire segment proximal loop attachment.

13. The stent according to claim 9 wherein the distal end of the first wire segment is attached to the second wire segment forming a first wire segment distal loop attachment, the distal end of the second wire segment is attached to the first wire segment of an adjoining element or to the second wire segment of an adjoining element forming a second wire segment distal loop attachment.

14. The stent according to claim 9 wherein the proximal end of the strut is affixed to a location on the second wire segment distal to the first wire segment proximal loop attachment, the distal end of the strut is attached to a location on the second wire segment distal to the first wire segment distal loop attachment.

15. The stent according to claim 9 wherein the first and second wire segment proximal and distal loop attachments, and the strut proximal and distal loop attachments could be made by manually looping or by twisting, or by biocompatible adhesive, or by brazing, or by crimping, or by welding or by stamping.

* * * * *